(12) United States Patent
Aburdeineh et al.

(10) Patent No.: US 8,158,171 B2
(45) Date of Patent: Apr. 17, 2012

(54) METHODS OF LOWERING BLOOD CHOLESTEROL VIA ORAL FENUGREEK SEED EXTRACT COMPOSITIONS

(76) Inventors: S. George Aburdeineh, Falls Church, VA (US); Hikmat George Aburdeineh, Bethlehem (IL)

( * ) Notice: Subject to any disclaimer, the term of this patent is extended or adjusted under 35 U.S.C. 154(b) by 926 days.

(21) Appl. No.: 12/222,158

(22) Filed: Aug. 4, 2008

(65) Prior Publication Data

US 2008/0299235 A1    Dec. 4, 2008

Related U.S. Application Data

(63) Continuation-in-part of application No. 11/030,886, filed on Jan. 10, 2005.

(60) Provisional application No. 60/535,731, filed on Jan. 10, 2004.

(51) Int. Cl.
| | | |
|---|---|---|
| *A61K 131/00* | (2006.01) | |
| *A61K 36/48* | (2006.01) | |
| *A61P 43/00* | (2006.01) | |
| *A61P 3/06* | (2006.01) | |

(52) U.S. Cl. ............... 424/757; 424/756; 514/7.4

(58) Field of Classification Search .............. None
See application file for complete search history.

(56) References Cited

U.S. PATENT DOCUMENTS

| | | |
|---|---|---|
| 4,834,990 A | 5/1989 | Amer |
| 5,009,819 A | 4/1991 | Popescu et al. |
| 5,558,897 A | 9/1996 | Goldman |
| 5,851,578 A | 12/1998 | Gandhi |
| 7,338,675 B2 | 3/2008 | Lee et al. |

*Primary Examiner* — Michele C. Flood
(74) *Attorney, Agent, or Firm* — Raj Bawa; Bawa Biotech LLC

(57) ABSTRACT

A method of lowering blood cholesterol in a non-diabetic human patient by at least 30% is described. The method involves orally administering for 30 consecutive days a fenugreek seed extract composition. Various methods of preparation and various formulations are described. Agents such as pharmaceutically acceptable excipients, lubricants, binders, glidants, fillers, flavoring agents, vitamins, minerals, active agents other than fenugreek, herbal extracts other than fenugreek, carriers and mixtures thereof may be additionally incorporated into the fenugreek seed extract composition. Physiologically effective dosage forms (liquid and solid) containing fenugreek seed extract compositions are also disclosed.

18 Claims, No Drawings

METHODS OF LOWERING BLOOD CHOLESTEROL VIA ORAL FENUGREEK SEED EXTRACT COMPOSITIONS

CROSS-REFERENCE TO RELATED APPLICATIONS

This application is a continuation-in-part application of parent U.S. application Ser. No. 11/030,886 (filed Jan. 10, 2005), from which priority is claimed, the disclosure of which is totally incorporated herein by reference.

Also, parent U.S. application Ser. No. 11/030,886 claims benefit under 35 U.S.C. §119(e) of U.S. provisional patent application Ser. No. 60/535,731 (filed Jan. 10, 2004), which is incorporated herein by reference in its entirety.

FIELD OF THE INVENTION

The present invention relates to methods of lowering cholesterol, particularly of lowering blood cholesterol via fenugreek seed extracts and pharmaceutical compositions incorporating the same.

BACKGROUND OF THE INVENTION

The present invention is directed to relatively stable, convenient and patient-friendly compositions of fenugreek seed extract, including pharmaceutically acceptable compositions thereof. The invention further provides a method for preparing such compositions. The compositions of this invention are advantageously used in methods for treating a non-diabetic individual having a disorder associated with high cholesterol. Specifically, the present invention includes employing fenugreek seed extract, or compositions or formulations comprising them, to lower cholesterol in a non-diabetic to a greater degree compared to conventional preparations. Fenugreek seed extracts, or compositions or formulations comprising them, have several advantages, including: the capability of daily oral dosing, ease of use in suspension form, safety, efficacy, purity, relative stability, and resuspendability over a short period of time.

The invention relates to an extraction process that uses fenugreek, fenugreek extracts or grinds (herein referred to as "juice" or "extract"). The instant compositions also encompass carbonated or non-carbonated beverages and formulations containing the aforementioned fenugreek extract which may further contain minerals, vitamins, nutrients, standard excipients, carriers, physiologically active agents, etc. The formulation may be in a ready-to-drink form in a container, a concentrate, or as a powder mix to be reconstituted with water or other ingestible liquids. Moreover, it may be compounded in the form of a pill, capsule, granules, microparticles, nanoparticles or liposomes.

The instant inventors have discovered that treating non-diabetic human patients suffering from high cholesterol levels with the above-mentioned composition(s) significantly lowers the patient's cholesterol levels. While it may be anticipated that any soluble fiber may achieve a decrease in the blood cholesterol level (U.S. Pat. Nos. 4,834,990, 5,009,819, 5,558,897 and 5,851,578, incorporated herein by reference), the instant method yields the unexpected result of a 30% or more reduction in the blood cholesterol.

While the prior art generally discloses a reduction of several points using "juices" such as those of fenugreek often in the range of 5-15 points (which is in the general range of 2-10%), the inventors compositions(s) derived via the specific extraction process yields invariably reductions in the range of 30% or higher (Table 1). For instance, consuming little amounts of fenugreek "juice" of the instant invention over thirty days of consecutive usage provides dramatic results enumerated herein. This data is unprecedented in the literature. In fact, such a result is neither disclosed in the prior art nor would it be obvious to one of ordinary skill in the art.

As stated above, the present invention also provides a ready-to-drink beverage or a concentrate in a solid (e.g., powder mix) or a liquid form for reconstitution into a beverage. Furthermore, such beverages may be supplemented with soluble minerals (e.g., calcium), vitamins, soluble fibers, flavors, colors, adjuvants, taste-masking agents, conventional solvents and carriers.

Commercially marketed fiber-containing products are not often well received by patients with respect to taste and appearance of the final product at the time of consumption. The present invention alleviates these problems.

The present invention also has the advantage of simplicity of extraction. The present inventors have discovered that simply boiling fenugreek seeds in water results in an extraction (the "juice" or "extract") that can be directly employed in the claimed compositions to lower cholesterol to the specified degree.

Furthermore, the instant inventors have also noted the following benefits of using fenugreek "juice" (without any observed side effects):
1) alleviation of a woman's birth pains;
2) aiding women suffering from a lack of estrogen;
3) regulating menstrual period;
4) assisting in milk production in nursing women;
5) treating rheumatism;
6) treating cough and sore throat pain; and
7) acting as a sexual stimulant in women.

TABLE 1

| Case # | Age | Sex | Cholesterol levels prior to fenugreek treatment (mg/100 ml) | Cholesterol levels following one month of fenugreek treatment (mg/100 ml) | % Decrease | Cholesterol levels following three months of fenugreek treatment (mg/100 ml) | % Decrease | Cholesterol levels following one year of fenugreek treatment (mg/100 ml) | % Decrease |
|---|---|---|---|---|---|---|---|---|---|
| 1 | 33 | M | 320 | 280 | 12.5 | 240 | 25 | 190 | 40.6 |
| 2 | 41 | M | 280 | 220 | 21.4 | 180 | 35.7 | 150 | 46.4 |
| 3 | 48 | M | 330 | 280 | 15 | 240 | 27 | 180 | 45.5 |
| 4 | 57 | M | 285 | 255 | 10.5 | 215 | 24.6 | 205 | 28.1 |
| 5 | 52 | M | 337 | 245 | 27.3 | 200 | 40.7 | 165 | 51 |
| 6 | 44 | M | 295 | 265 | 10.2 | 215 | 27.1 | 198 | 33 |
| 7 | 48 | M | 305 | 285 | 7 | 255 | 16.4 | 204 | 33.1 |
| 8 | 39 | M | 440 | 380 | 13.6 | 285 | 35.2 | 205 | 53.4 |
| 9 | 65 | M | 276 | 245 | 11.2 | 205 | 25.7 | 155 | 43.8 |

TABLE 1-continued

| Case # | Age | Sex | Cholesterol levels prior to fenugreek treatment (mg/100 ml) | Cholesterol levels following one month of fenugreek treatment (mg/100 ml) | % Decrease | Cholesterol levels following three months of fenugreek treatment (mg/100 ml) | % Decrease | Cholesterol levels following one year of fenugreek treatment (mg/100 ml) | % Decrease |
|---|---|---|---|---|---|---|---|---|---|
| 10 | 58 | M | 288 | 238 | 17.4 | 220 | 23.6 | 210 | 27.1 |
| 11 | 48 | M | 305 | 245 | 19.7 | 185 | 39.3 | 175 | 42.6 |
| 12 | 47 | M | 265 | 245 | 7.5 | 235 | 11.3 | 215 | 18.9 |
| 13 | 55 | M | 276 | 266 | 3.6 | 260 | 5.8 | 235 | 14.9 |
| 14 | 62 | M | 457 | 352 | 23 | 320 | 30 | 265 | 42 |
| 15 | 27 | M | 305 | 265 | 13.1 | 255 | 16.4 | 210 | 31.1 |
| 16 | 55 | M | 330 | 290 | 12.1 | 260 | 21.1 | 199 | 39.7 |
| 17 | 25 | M | 345 | 245 | 29 | 235 | 32 | 225 | 35 |
| 18 | 36 | M | 294 | 230 | 22 | 210 | 29 | 189 | 36 |
| 19 | 47 | M | 282 | 252 | 11 | 222 | 21.3 | 185 | 34.4 |
| 20 | 32 | M | 288 | 232 | 19.4 | 210 | 27.1 | 155 | 46.2 |
| 21 | 53 | M | 270 | 235 | 13 | 215 | 20.4 | 195 | 28 |
| 22 | 60 | M | 284 | 235 | 17.3 | 185 | 35 | 175 | 38.4 |
| 23 | 61 | M | 295 | 245 | 17 | 215 | 27.1 | 200 | 32.2 |
| 24 | 33 | M | 340 | 240 | 29.4 | 200 | 41.2 | 192 | 44 |
| 25 | 22 | M | 290 | 210 | 27.6 | 190 | 34.5 | 182 | 37.2 |
| 26 | 42 | M | 287 | 255 | 11.1 | 220 | 23.3 | 185 | 35.5 |
| 27 | 60 | M | 290 | 265 | 8.6 | 240 | 17.2 | 185 | 36.2 |
| 28 | 58 | M | 280 | 270 | 3.6 | 230 | 17.9 | 220 | 21.4 |
| 29 | 40 | M | 275 | 245 | 10.9 | 220 | 20 | 185 | 32.7 |
| 30 | 32 | M | 455 | 380 | 16.5 | 290 | 36.3 | 220 | 51.6 |
| 31 | 45 | M | 295 | 220 | 25.4 | 190 | 35.6 | 170 | 42.4 |
| 32 | 43 | M | 270 | 245 | 9.3 | 210 | 22.2 | 200 | 26 |
| 33 | 24 | M | 290 | 265 | 8.6 | 210 | 27.6 | 195 | 32.8 |
| 34 | 47 | M | 290 | 245 | 15.5 | 205 | 29.3 | 175 | 39.7 |
| 35 | 45 | M | 297 | 265 | 10.8 | 220 | 26 | 200 | 32.7 |
| 36 | 51 | M | 330 | 285 | 13.6 | 245 | 25.8 | 199 | 40 |
| 37 | 47 | M | 280 | 210 | 25 | 200 | 28.6 | 185 | 40 |
| 38 | 78 | M | 295 | 235 | 20.3 | 215 | 27.1 | 193 | 34.6 |
| 39 | 41 | M | 260 | 210 | 19.2 | 200 | 23.1 | 185 | 29 |
| 40 | 29 | M | 299 | 236 | 21.1 | 205 | 31.5 | 198 | 33.8 |
| 41 | 16 | M | 355 | 285 | 19.8 | 220 | 38 | 195 | 45.1 |
| 42 | 46 | M | 298 | 256 | 14.1 | 225 | 24.5 | 205 | 31.2 |
| 43 | 24 | M | 270 | 225 | 16.7 | 205 | 24 | 200 | 26 |
| 44 | 45 | M | 260 | 215 | 17.3 | 195 | 25 | 180 | 30.8 |
| 45 | 41 | M | 250 | 210 | 16 | 200 | 20 | 190 | 24 |
| 46 | 55 | M | 270 | 245 | 9.3 | 215 | 20.4 | 195 | 27.8 |
| 47 | 28 | M | 280 | 250 | 10.7 | 210 | 25 | 200 | 28.6 |
| 48 | 22 | M | 310 | 290 | 6.5 | 245 | 20.9 | 198 | 36.1 |
| 49 | 35 | M | 295 | 290 | 0 | 310 | 0 | 295 | 0 |
| 50 | 48 | M | 345 | 355 | 0 | 340 | 0 | 348 | 0 |
| 51 | 55 | M | 295 | 298 | 0 | 290 | 0 | 310 | 0 |
| 52 | 45 | M | 280 | 280 | 0 | 275 | 0 | 285 | 0 |
| 53 | 38 | F | 390 | 320 | 18 | 260 | 33.3 | 230 | 41 |
| 54 | 41 | F | 355 | 280 | 21.1 | 220 | 38 | 185 | 47.9 |
| 55 | 42 | F | 450 | 350 | 22.2 | 320 | 28.9 | 230 | 48.9 |
| 56 | 47 | F | 290 | 270 | 6.9 | 220 | 24.1 | 175 | 39.7 |
| 57 | 55 | F | 425 | 375 | 11.8 | 325 | 23.5 | 240 | 43.5 |
| 58 | 45 | F | 335 | 285 | 14.9 | 265 | 20.9 | 185 | 44.8 |
| 59 | 43 | F | 296 | 221 | 25.3 | 185 | 37.5 | 155 | 47.6 |
| 60 | 35 | F | 270 | 245 | 9.2 | 205 | 24.1 | 145 | 46.3 |
| 61 | 32 | F | 265 | 205 | 22.7 | 165 | 37.7 | 110 | 58.5 |
| 62 | 31 | F | 260 | 195 | 25 | 175 | 32.7 | 135 | 48.1 |
| 63 | 37 | F | 245 | 195 | 20.4 | 155 | 36.7 | 125 | 49 |
| 64 | 35 | F | 280 | 240 | 14.3 | 192 | 31.4 | 180 | 35.7 |
| 65 | 49 | F | 285 | 220 | 22.8 | 210 | 26.3 | 205 | 28.1 |
| 66 | 56 | F | 295 | 215 | 27.1 | 205 | 30.5 | 185 | 37.3 |
| 67 | 41 | F | 268 | 210 | 21.6 | 196 | 26.9 | 145 | 45.9 |
| 68 | 46 | F | 295 | 255 | 13.6 | 195 | 33.9 | 190 | 35.6 |
| 69 | 59 | F | 278 | 244 | 12.2 | 215 | 22.7 | 202 | 27.3 |
| 70 | 55 | F | 245 | 185 | 24.5 | 155 | 36.7 | 135 | 44.9 |
| 71 | 50 | F | 560 | 495 | 11.6 | 432 | 22.9 | 298 | 46.8 |
| 72 | 66 | F | 332 | 285 | 14.2 | 234 | 29.5 | 200 | 39.8 |
| 73 | 44 | F | 260 | 220 | 15.4 | 195 | 25 | 165 | 36.5 |
| 74 | 59 | F | 290 | 240 | 17.2 | 195 | 32.8 | 165 | 43.1 |
| 75 | 37 | F | 305 | 205 | 32.8 | 175 | 42.6 | 155 | 49.2 |
| 76 | 69 | F | 295 | 265 | 10.2 | 210 | 28.8 | 200 | 32.2 |
| 77 | 55 | F | 275 | 255 | 7.3 | 215 | 21.8 | 195 | 29.1 |
| 78 | 24 | F | 290 | 230 | 20.7 | 198 | 31.7 | 170 | 41.4 |
| 79 | 47 | F | 310 | 265 | 14.5 | 245 | 21 | 200 | 35.5 |
| 80 | 48 | F | 270 | 210 | 22.2 | 190 | 29.6 | 180 | 33.3 |
| 81 | 38 | F | 310 | 255 | 17.7 | 220 | 29 | 185 | 40.3 |

TABLE 1-continued

| Case # | Age | Sex | Cholesterol levels prior to fenugreek treatment (mg/100 ml) | Cholesterol levels following one month of fenugreek treatment (mg/100 ml) | % Decrease | Cholesterol levels following three months of fenugreek treatment (mg/100 ml) | % Decrease | Cholesterol levels following one year of fenugreek treatment (mg/100 ml) | % Decrease |
|---|---|---|---|---|---|---|---|---|---|
| 82 | 57 | F | 277 | 210 | 24.2 | 185 | 33.2 | 155 | 44 |
| 82 | 33 | F | 288 | 245 | 14.9 | 198 | 31.3 | 185 | 35.8 |
| 84 | 68 | F | 280 | 200 | 28.6 | 192 | 31.4 | 165 | 41.1 |
| 85 | 44 | F | 285 | 255 | 10.5 | 210 | 26.3 | 195 | 31.6 |
| 86 | 37 | F | 275 | 225 | 18.2 | 205 | 25.5 | 173 | 37.1 |
| 87 | 82 | F | 310 | 255 | 17.7 | 225 | 27.4 | 196 | 36.8 |
| 88 | 75 | F | 286 | 255 | 10.8 | 210 | 26.6 | 200 | 30.1 |
| 89 | 53 | F | 265 | 210 | 20.8 | 195 | 26.4 | 190 | 28.3 |
| 90 | 42 | F | 280 | 255 | 8.9 | 220 | 21.4 | 200 | 28.6 |
| 91 | 47 | F | 291 | 240 | 17.5 | 210 | 27.8 | 195 | 33 |
| 92 | 77 | F | 295 | 265 | 10.2 | 225 | 23.7 | 195 | 33.9 |
| 93 | 44 | F | 288 | 265 | 8 | 235 | 18.4 | 215 | 25.3 |
| 94 | 48 | F | 350 | 285 | 18.6 | 235 | 32.9 | 200 | 42.9 |
| 95 | 52 | F | 285 | 235 | 17.5 | 200 | 29.8 | 175 | 38.6 |
| 96 | 39 | F | 275 | 245 | 10.9 | 215 | 21.8 | 200 | 27.3 |
| 97 | 57 | F | 265 | 210 | 20.8 | 200 | 24.5 | 180 | 30.1 |
| 98 | 28 | F | 285 | 285 | 0 | 275 | 0 | 290 | 0 |
| 99 | 62 | F | 315 | 310 | 0 | 320 | 0 | 305 | 0 |

DETAILED DESCRIPTION OF THE INVENTION

In this specification, although the preferred embodiments have been described in detail, it should be understood that various changes, substitutions and alterations may be made therein without departing from the spirit and scope of the invention. Therefore, the specification is to be regarded in an illustrative rather than a restrictive sense. In other words, the described embodiments of the invention and the disclosed examples are given for the purpose of illustration rather than limitation of the invention as set forth in the appended claims.

Unless otherwise defined herein, scientific and technical terms used in connection with the present invention shall have the meanings that are commonly understood by those of ordinary skill in the art. The use of the terms "a", "an", and "the" in the context of describing the invention (especially in the context of the claims recited herein) are to be construed to cover both the singular and the plural, unless otherwise indicated herein or clearly contradicted by context. Furthermore, unless otherwise required by context, singular terms shall include pluralities and plural terms shall include the singular. Generally, nomenclatures used in connection with, and standard techniques described herein are those well known and commonly used in the art. Unless stated to the contrary, any use of the words such as "including," "containing," "comprising," "having" and the like, means "including without limitation" and shall not be construed to limit any general statement that it follows to the specific or similar items or matters immediately following it.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

For millennia, fenugreek (*Trigonella foenum graecum*) has been used both as a medicine and as a food spice in India and the Middle East. Fenugreek is cultivated worldwide as a semi-arid crop and its seeds have been used for centuries by practitioners of Indian Ayurvedic medicine as well as traditional Chinese Medicine. The fenugreek plant is native to the Mediterranean areas of Europe and to India. Fenugreek is commonly known as Methi (Punjab, India) or Hilbeh (Arabic) and is used both as an herb (the leaves) and as a spice (the seed). Charred fenugreek seeds have been recovered from Tell Halal (Iraq) dating to 4000 BC and as desiccated seeds from the tomb of Tutankhamen (Egypt).

Fenugreek is generally regarded as safe and non-toxic. In India its leaves are cooked as a vegetable and also used as animal feed. Fresh seeds are often used as flavoring or sprouted and eaten as a salad green. Fenugreek seeds have a slight maple taste and are often used in production of imitation maple flavorings. The fenugreek plant produces small white flowers in late summer and after the flowers die, large pods that contain 10-20 irregularly-shaped yellow seeds develop. In some parts of the world, dried fenugreek seeds are ground for a curry spice. However, they may also be boiled to produce a yellow dye, roasted as a coffee substitute, or used to flavor foods and tobacco. After the seeds are collected from the plants, the plants may be chopped and used as fertilizer.

Recent interest in fenugreek focuses on its potential benefits to lower blood sugar in diabetics. In some individuals dietary intake of soluble fiber can slow absorption and subsequent digestion of food that results in a slower rise in blood sugar levels. Some clinical studies have demonstrated that fenugreek seeds reduce blood glucose levels and decrease insulin resistance in mild type-2 diabetic patients. Fenugreek contains the amino acid, 4-hydroxyisoleucine, which appears to increase the body's production of insulin when blood sugar levels are elevated.

Studies have also shown that fenugreek may lower levels of triglycerides and serum cholesterol levels in diabetics. In terms of weight control, the soluble fiber in fenugreek seeds can reduce dietary fat absorption by binding to fatty acids as well as create a sensation of "fullness," thereby reducing appetite. Finally, because fenugreek seeds contain estrogen-like saponins, blood levels of total cholesterol, LDL and triglycerides can be reduced (with no change in HDL). Although it is by no means the only major risk factor, elevated serum cholesterol is associated with a greater risk of heart disease. Cholesterol levels under 200 mg/dl are considered optimal. However, a low cholesterol level is not any guarantee of good heart health as some people with low cholesterol levels do suffer heart attacks. Evaluation of changes in cholesterol requires consultation with a healthcare professional and should include measurement of total serum cholesterol, as well as HDL and LDL cholesterol. The present inventors observed no side effects or poisoning as a result of orally consuming the fenugreek "juice," even if done in large quantities. In fact, it was observed that doping or consuming mega-doses has no effect as compared to lower doses. The inventors found that amounts as little as two ounces per day for 30 days provided the unexpected therapeutic effect of a reduction of blood cholesterol by at least 30%. Other patients consumed as much as about five cups a day to derive the identical beneficial effect.

Fenugreek seed extracts may also have other medical uses. It may reduce the amounts of calcium oxalate in the kidneys, often a contributing factor in kidney stones. In animal studies, fenugreek also appeared to lessen the chance of developing colon cancer by blocking the action of certain enzymes. Topically, the gelatinous texture of fenugreek seed may have some benefit for soothing skin that is irritated by eczema or other conditions. It has also been applied as a warm poultice to relieve muscle aches and gout pain. To be applied topically, fenugreek seeds can be ground into a powder, and then soaked in hot water to form a thick gel. Fenugreek is a mild but effective laxative.

The instant fenugreek extract or "juice" can be combined with any pharmaceutically acceptable excipient. According to this invention, a "pharmaceutically acceptable excipient" is an excipient that acts as filler or a combination of fillers used in pharmaceutical compositions. Preferred excipients included in this category are: 1) amino acids, such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-beta-cyclodextrin; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. Salts of such compounds may also be used.

This invention advantageously permits consumption of the instant fenugreek extract or "juice" by a human. In one embodiment, the compositions according to this invention are administered about once a day. In another embodiment, the compositions according to this invention are administered about once a day for a month. In yet another embodiment, the compositions according to this invention are administered for a period longer than a month. It will be appreciated by those of skill in the art that the specific treatment regimen will depend upon factors such as the cholesterol level in the patient, the age and weight of the patient to be treated, the general physical condition of the patient and the judgment of the treating physician.

By "oral dosage form" is meant to include a unit dosage form prescribed or intended for oral administration. An oral dosage form may or may not comprise a plurality of subunits such as, for example, microcapsules or microtablets, packaged for administration in a single dose. The term "dosage form" denotes a form of a formulation that contains an amount sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics such as solubility, and with the characteristics of the swellable matrix such as its permeability, and the relative amounts of the drug and polymer. The dosage form can be prepared by various conventional mixing, comminution and fabrication techniques readily apparent to those skilled in the chemistry of drug formulations.

Certain oral dosage forms described herein may be "coated". The coating can be a functional or a non-functional coating, or multiple functional and/or non-functional coatings. By "functional coating" is meant to include a coating that modifies the release properties of the total formulation, for example, a sustained-release coating. By "non-functional coating" is meant to include a coating that is not a functional coating. Note that a non-functional coating can have some impact on the release of the active agent due to the initial dissolution, hydration or perforation of the coating but would not be considered to be a significant deviation from the non-coated composition. Enteric coated formulations, which protect the stomach against any irritant effects of the active agent(s), are also possible within the scope of this invention. Such formulations can be coated with a composition that is non-toxic and includes a pharmaceutically acceptable enteric polymer which is predominantly soluble in the intestinal fluid while being substantially insoluble in the low pH of the gastric juices. Examples include polyvinyl acetate phthalate (PVAP), hydroxypropylmethyl-cellulose acetate succinate (HPMCAS), cellulose acetate phthalate (CAP), methacrylic acid copolymer, hydroxy propyl methylcellulose succinate, cellulose acetate succinate, cellulose acetate hexahydrophthalate, hydroxypropyl methylcellulose hexahydrophthalate, hydroxypropyl methylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer (acid number 300 to 330) and also known as EUDRAGIT L, which is an anionic copolymer based on methacrylate and available as a powder (also known as methacrylic acid copolymer, type A NF), methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin bearing carboxyl groups. The methacrylic acid: acrylic acid ethyl ester 1:1 copolymer solid substance of the acrylic dispersion sold under the trade designation "EUDRAGIT L-100-55" may be suitable.

The phrase "active agent other than fenugreek" is meant to include solvates (including hydrates) of any active agent or its salts, crystalline and non-crystalline forms, as well as various polymorphs. This phrase may also include cholesterol lowering drugs (other than fenugreek) or a pharmaceutically acceptable salt or optical isomer thereof.

"Pharmaceutically acceptable salts" includes derivatives of the active agents, wherein the parent compound is modified by making non-toxic acid or base salts addition thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric, etc.; other acceptable inorganic salts include metal salts such as sodium salt, potassium salt, cesium salt, etc.; and alkaline earth metal salts, such as calcium salt, magnesium salt, etc., and combinations comprising one or more of the foregoing salts. Pharmaceutically acceptable organic salts includes salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like; organic amine salts such as triethylamine salt, pyridine salt, picoline salt, ethanolamine salt, triethanolamine salt, dicyclohexylamine salt, N,N.-dibenzylethylenediamine salt, and the like; and amino acid salts such as arginate, asparginate, glutamate, and the like; and combinations comprising one or more of the foregoing salts.

The phrase "water-soluble fenugreek seed extract" implies a composition that is at least slightly water-soluble (for example, about 1 to about 10 mg/ml at 25° C.). On the other hand, a "water-insoluble fenugreek seed extract" implies a composition that has a water solubility of less than 1 mg/ml.

Examples of suitable lubricants include stearic acid, magnesium stearate, glyceryl behenate, talc, mineral oil (in PEG), and combinations comprising one or more of the foregoing lubricants. Examples of suitable binders include water-soluble polymer, such as modified starch, gelatin, polyvinylpyrrolidone, polyvinyl alcohol, and combinations comprising one or more of the foregoing lubricants. An example of a glidant is silicon dioxide (AEROSIL, Degussa). Suitable fillers include insoluble materials such as silicon dioxide, titanium dioxide, talc, alumina, starch, kaolin, polacrilin potassium, powdered cellulose, and microcrystalline cellulose, and combinations comprising one or more of the foregoing fillers. Soluble fillers include, for example, mannitol, sucrose, lactose, dextrose, sodium chloride, sorbitol, and combinations comprising one or more of the foregoing fillers.

It should also be understood that the various embodiments of the present invention are not mutually exclusive, but may be implemented in various combinations.

In order that this invention may be better understood, the following examples are set forth. These examples are for the purpose of illustration only and are not to be construed as limiting the scope of the invention in any manner. Numerous other variations of the present invention will be appreciated by those skilled in the art, in view of the disclosure herein. The exact compositions, methods of preparation and embodiments shown are not limiting of the invention, and any obvious modifications will be apparent to one skilled in the art.

EXAMPLE 1

Extraction may be carried out in one of the following three Ways:
Simple Extraction Soak about ⅓ cup of fenugreek seeds in about 15 cups of water for 8-10 hours. Bring the mixture to a boil for about 5-7 minutes. Cool, strain and refrigerate the extracted "juice."
Quick Extraction Combine about ⅓ cup fenugreek seeds in about 15 cups of water and bring to a boil for about 10 minutes. Cool, strain and refrigerate the extracted "juice."
Preferred Extraction Grind about ⅓ cup of fenugreek seed to a powder. Combine the resulting powder with about 15 cups of water and bring to a boil for 10 minutes. Cool, strain and refrigerate the extracted "juice."
Note: The noted boiling times above are only preferred embodiments and may be considerably shorter or longer. Similarly, the proportion of seed to water employed may be scaled appropriately. The simple extraction method described above produces a slightly more opaque product. The best way to store fenugreek is to keep the seed in a cool and dry place. This allows for it to be kept for several months without loss in activity. Once the seed is ground or powdered, it does not keep well and must be used promptly. As soon as the "juice" is extracted, whether from the seed or the grind, it is preferred that it be kept refrigerated prior to consumption or further processing to reformulate it into a dosage form, etc.

EXAMPLE 2

Reconstitution of the extracted "Juice" may be accomplished by the following method:

As stated earlier, while the exact composition of the final beverage may be in the form of the extracted "juice," tea or carbonated beverage, a small quantity taken each day for 30 consecutive days provides a reduction in blood cholesterol of 30% or more. An individual serving of tea may be prepared by boiling a teaspoon of fresh powdered/ground fenugreek seeds in a cup of water for ten minutes. Appropriate flavors, conventional carriers, excipients or additives may be additionally incorporated into the extracted "juice." Examples include sweeteners (e.g., honey, sugar, aspartame, etc.) or flavors (e.g., lemon, anise, mint, etc.). Additionally, these beverages may be supplemented with various nutrients, vitamins, minerals, pharmaceutically active agents, fibers and herbal extracts. The extracted "juice" (fenugreek seed extract composition) can be compounded into solid dosage forms, including enteric dosage forms.

However, it is understood that the invention is not limited to the disclosed compositions, methods of preparation and embodiments shown, including any embodiments that may be apparent to one of ordinary skill in the art. Although the foregoing invention has been described in some detail by way of illustration and examples for purposes of clarity of understanding, it will be readily apparent to those of ordinary skill in the art in light of the teachings of this invention that certain variations and modifications may be made thereto without departing from the spirit or scope of the disclosure herein, including the specific embodiments.

We claim:

1. A method of lowering blood cholesterol in a non-diabetic human patient by at least 30% consisting of orally administering for at least 30 consecutive days to a non-diabetic human patient in need thereof an effective amount of a fenugreek (*Trigonella foenum graecum*) seed extract composition prepared by
   (a) grinding approximately ⅓ cup of dry fenugreek seeds to obtain a powder;
   (b) combining the powder with 15 cups of water to obtain a mixture;
   (c) boiling the mixture for at least 10 minutes to obtain a boiled mixture;
   (d) cooling the boiled mixture to room temperature to obtain a cooled mixture;
   (e) straining the cooled mixture;
   (f) recovering the strained mixture to obtain a fenugreek seed extract composition;
   (g) refrigerating the fenugreek seed extract composition;
   and (h) orally delivering a dose of the fenugreek seed extract composition to the human patient, wherein said dose is delivered via a dose regimen selected from the group consisting of about two ounces a day, about five cups a day, about three cups a day, and about one to two cups a day.

2. The method of claim 1 further comprising adding an agent to the fenugreek seed extract composition, wherein the agent is selected from the group consisting of a pharmaceutically acceptable excipient, lubricant, binder, glidant, filler, flavoring agent, vitamin, mineral, active agent other than fenugreek, herbal extract other than fenugreek, a carrier and mixtures thereof.

3. A method of lowering blood cholesterol in a non-diabetic human patient by at least 30% consisting of administering an effective amount of an oral dosage form for at least 30 consecutive days to a non-diabetic human patient in need thereof, wherein the oral dosage form consists of an effective amount of a water soluble fenugreek (*Trigonella foenum graecum*) seed extract composition prepared by
   (a) grinding approximately ⅓ cup of dry fenugreek seeds to obtain a powder;
   (b) combining the powder with 15 cups of water to obtain a mixture;
   (c) boiling the mixture for at least 10 minutes;
   (d) cooling the mixture of (c) to room temperature to obtain a cooled mixture;
   (e) straining the cooled mixture;
   (f) recovering the mixture of (e) to obtain a fenugreek seed extract composition;
   (g) adding an agent to the fenugreek seed extract composition of (f), wherein the agent is selected from the group consisting of a pharmaceutically acceptable excipient, lubricant, binder, glidant, filler, flavoring agent, masking agent, vitamin, mineral, active agent other than fenugreek, herbal extract other than fenugreek, a carrier and mixtures thereof; and
   (h) compounding the fenugreek seed extract composition of (g) in the form of an oral dosage form selected from the group consisting of a pill, capsule, caplet granules, microparticles, nanoparticles, liquid and liposomes.

4. The method according to claim 3, wherein the oral dose is a liquid and the administering is according to a dose regimen selected from the group consisting of (a) about two ounces a day; (b) about five cups a day; (c) about three cups a day; and, (d) about one to two cups a day.

5. The method according to claim 3, wherein the oral dose is a liquid and the administering is according to a dose regimen selected from the group consisting of (a) about two ounces a day for 1-12 months; (b) about five cups a day for 1-12 months; (c) about three cups a day for 1-12 months; and (d) about one to two cups a day for 1-12 months.

6. The method of claim 3, wherein the oral dosage form is a single dose solid enteric coated formulation.

7. The method of claim 3, wherein the oral dosage form is a liquid oral liposomal formulation.

8. The method of claim 3, wherein the oral dosage form contains a plurality of therapeutic nanoparticles.

9. The method of claim 3, where the flavoring agent is selected from the group consisting of lemon, anise and mint.

10. The method of claim 3, where the masking agent is selected from the group consisting of honey, sugar and aspartame.

11. The method of claim 3, wherein the active agent is a cholesterol lowering drug or a pharmaceutically acceptable salt thereof.

12. The method according to claim 1, wherein the composition is administered to the patient by a dose regimen selected from the group consisting of
    (a) about two ounces a day for 1-12 months;
    (b) about five cups a day for 1-12 months;
    (c) about three cups a day for 1-12 months; and
    (d) about one to two cups a day for 1-12 months.

13. The method of claim 1, further comprising adding to the fenugreek seed extract composition a sweetener selected from the group consisting of honey, sugar and aspartame and a flavor selected from the group consisting of lemon, anise and mint.

14. The method of claim 13 further comprising adding carbonation to produce a carbonated beverage.

15. A method of lowering blood cholesterol in a non-diabetic human patient by at least 30% consisting of orally administering for at least 30 consecutive days to a non-diabetic human patient in need thereof an effective amount of a fenugreek (*Trigonella foenum graecum*) seed extract composition prepared by the method consisting essentially of the following sequential steps:
    (a) grinding approximately ⅓ cup of dry fenugreek seeds to obtain a powder;
    (b) combining the powder obtained in (a) with about 15 cups of water to obtain a mixture;
    (c) boiling the mixture of (b) for at least 10 minutes;
    (d) cooling the mixture of (c) to room temperature to obtain a cooled mixture;
    (e) straining the cooled mixture of (d);
    (f) recovering the mixture of (e) to obtain a fenugreek seed extract composition;
    (g) refrigerating the fenugreek seed extract composition of step (f);
    (h) optionally adding an agent to the fenugreek seed extract composition of (g) selected from the group consisting of a pharmaceutically acceptable excipient, lubricant, binder, glidant, filler, flavoring agent, vitamin, mineral, active agent other than fenugreek, herbal extract other than fenugreek, a carrier and mixtures thereof; and
    (i) orally delivering a dose of the composition of (g) to the human patient, wherein said dose is delivered via a dose regimen selected from the group consisting of about two ounces a day, about five cups a day, about three cups a day, and about one to two cups a day.

16. The method according to claim 15, wherein the oral dosage form is administered according to a dose regimen selected from the group consisting of:
    (a) about two ounces a day for 30 days to 12 months;
    (b) about five cups a day for 30 days to 12 months;

(c) about three cups a day for 30 days to 12 months; and
(d) about one to two cups a day for 30 days to 12 months.

17. The method of claim 15, further comprising, following refrigerating of (g), adding carbonation to produce a carbonated beverage.

18. The method of claim 15, further comprising, following refrigerating of (g), adding a fruit juice to the fenugreek seed extract seed composition.

* * * * *